United States Patent [19]

Miyake et al.

[11] Patent Number: 5,202,324

[45] Date of Patent: Apr. 13, 1993

[54] IMIDAZOPYRIDAZINES

[75] Inventors: Akio Miyake, Hirakata; Masaaki Kuwahara, Itami; Hisashi Kuriki, Kawanishi, all of Japan

[73] Assignee: Takeda Chemical Industries, Ltd., Osaka, Japan

[21] Appl. No.: 472,804

[22] Filed: Jan. 31, 1990

[30] Foreign Application Priority Data

Jan. 31, 1989 [JP] Japan ............................. 1-023355
Dec. 29, 1989 [JP] Japan ............................. 1-0342258

[51] Int. Cl.$^5$ .................. A61K 31/50; A61K 31/535; A61K 31/55; C07D 487/04
[52] U.S. Cl. .......................... 514/248; 514/211; 514/212; 514/218; 514/222.2; 514/226.8; 514/228.5; 514/228.8; 514/232.2; 514/254; 540/545; 540/546; 540/553; 540/575; 540/599; 544/61; 544/117; 544/236
[58] Field of Search .................. 544/236, 117, 61; 514/254, 211, 212, 218, 222.2, 226.8, 228.5, 228.8, 233.2, 248; 540/599, 575, 553, 546, 545

[56] References Cited

U.S. PATENT DOCUMENTS

| | | | |
|---|---|---|---|
| 4,330,543 | 5/1982 | Baldwin et al. | 514/248 X |
| 4,353,903 | 10/1982 | Fabiane et al. | 514/248 |
| 4,464,372 | 8/1984 | Baldwin et al. | 544/236 X |
| 5,145,850 | 9/1992 | Miyake et al. | 514/248 |

FOREIGN PATENT DOCUMENTS

| | | | |
|---|---|---|---|
| 0164252 | 6/1985 | European Pat. Off. | 544/236 |
| 0203271 | 3/1986 | European Pat. Off. | 544/236 |
| 0185346 | 6/1986 | European Pat. Off. | 544/236 |
| 0225522 | 6/1987 | European Pat. Off. | 544/236 |
| 0238070 | 9/1987 | European Pat. Off. | 544/236 |
| 0305093 | 3/1989 | European Pat. Off. | 544/236 |
| 2820938 | 11/1978 | Fed. Rep. of Germany | 544/236 |
| 64-40489 | 9/1983 | Japan | 544/236 |
| WO-8901478 | 2/1989 | PCT Int'l Appl. | 544/236 |
| 1135893 | 12/1968 | United Kingdom | 544/236 |

OTHER PUBLICATIONS

Morrison & Boyd, Organic Chemistry, 5th Ed., Allyn and Bacon, Inc., Boston, (1987) (1959), pp. 702, 703, 953.

Primary Examiner—Floyd D. Higel
Attorney, Agent, or Firm—Wegner, Cantor, Mueller & Player

[57] ABSTRACT

The imidazo[1,2-b]pyridazine compounds of the formula:

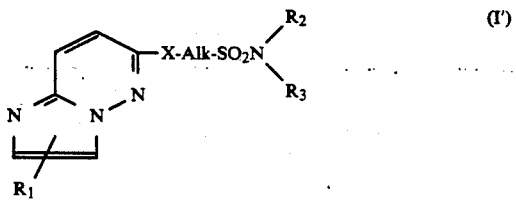

wherein $R_1$ is a hydrogen or halogen atom, or a lower alkyl group optionally having substituent(s), $R_2$ and $R_3$ are, independently, a hydrogen atom, a lower alkyl group optionally having substituent(s), a cycloalkyl group or a phenyl group optionally having substituent(s) or $R_2$ and $R_3$ together with the adjacent nitrogen atom to which they bond may form a heterocyclic ring optionally having substituent(s), X is an oxygen atom or $S(O)_n$ (n=0 to 2), Alk is a straight or branched chain alkylene group containing 1–10 carbon atoms and optionally having substituent(s), or their pharmaceutically acceptable salts which possess antiallergic, anti-inflammatory and anti-PAF activities, and their production and use.

20 Claims, No Drawings

IMIDAZOPYRIDAZINES

BACKGROUND OF THE INVENTION

1. Field of the Invention

This invention relates to novel imidazopyridazine derivatives, their production and use.

The imidazopyridazine derivatives of the invention possess antiallergic, anti-inflammatory and anti-PAF (platelet-activating factor) activities and are useful as antiasthmatics by controlling bronchospasm and bronchoconstriction.

2. Description of the Prior Art

It has been disclosed in Japanese Unexamined Patent Publication No. SHO 61(1986)-152684 that imidazo[1,2-b]pyridazine compounds show anti-thrombogenic activity as well as cardiovascular activity, especially cardiotonic activity. However, any imidazo[1,2-b]pyridazine derivative possessing antiallergic, anti-inflammatory and anti-PAF activities has not been reported.

On the other hand, it is desired to develop more effective antiasthmatics, although various kinds of antiasthmatics have been launched into markets.

As the result of extensive studies on chemical modification at the 6 position of imidazo[1,2-b] pyridazine, the inventors of this invention have found imidazo[1,2-b]pyridazine derivatives possessing antiallergic, anti-inflammatory and anti-PAF activities which are not reported so far in the existing imidazo[1,2-b]pyridazine compounds. Said derivatives have been also found to control bronchospasm and bronchoconstriction.

Thus, this invention has been completed.

SUMMARY OF THE INVENTION

The invention provides an imidazo [1,2-b]pyridazine compound of the formula (I):

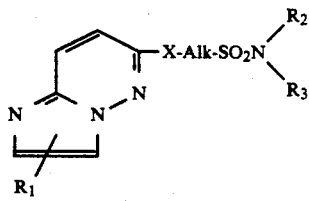
(I)

wherein $R_1$ is a hydrogen or halogen atom, or a lower alkyl group optionally having substituent(s), $R_2$ and $R_3$ are, independently, a hydrogen atom, a lower alkyl group optionally having substituent(s), a cycloalkyl group or a phenyl group optionally having substituent(s) or $R_2$ and $R_3$ together with the adjacent nitrogen atom to which they bond may form a heterocyclic ring optionally having substituent(s), X is an oxygen atom or $S(O)_n$ (n is 0 to 2), Alk is a straight or branched chain alkylene group containing 1-10 carbon atoms and optionally having substituent(s), provided that X should be an oxygen atom when $R_1$ is a hydrogen atom, one of $R_2$ and $R_3$ is a hydrogen atom and the remaining one is a hydrogen atom or a lower alkyl group and Alk is a straight chain alkylene group containing 2-4 carbon atom, or its salt.

Also, it provides an antiasthmatic composition which comprises a compound of the formula (I'):

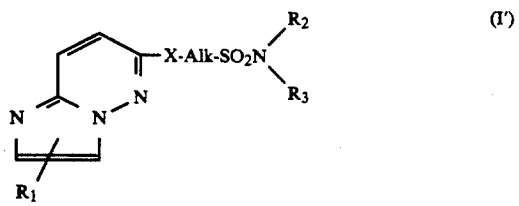

wherein $R_1$ is a hydrogen or halogen atom, or a lower alkyl group optionally having substituent(s), $R_2$ and $R_3$ are, independently, a hydrogen atom, a lower alkyl group optionally having substituent(s), a cycloalkyl group or a phenyl group optionally having substituent(s) or $R_2$ and $R_3$ together with the adjacent nitrogen atom to which they bond may form a heterocyclic ring optionally having substituent(s), X is an oxygen atom or $S(O)_n$ (n is 0 to 2), Alk is a straight or branched chain alkylene group containing 1-10 carbon atoms and optionally having substituent(s), or its salt.

Further, it provides a process for the production of a compound of the formula (I) or (I'), or its salt. When the compounds of the formula (I) or (I') contain an asymmetric carbon atom, their optionally active compounds and racemic mixtures are also included in the invention.

PREFERRED EMBODIMENTS OF THE INVENTION

The term "lower alkyl group" as used in the specification means a straight of branched chain alkyl group containing 1-6 carbon atoms. Examples of the lower alkyl groups are methyl, ethyl, n-propyl, i-propyl, tert-butyl, n-pentyl and n-hexyl.

The term "cycloalkyl group" means a cycloalkyl group containing 3-6 carbon atoms. Examples of the cycloalkyl groups are cyclopropyl, cyclobutyl, cyclopentyl and cyclohexyl.

Examples of the term "straight or branched chain alkylene group containing 1-10 carbon atoms" are

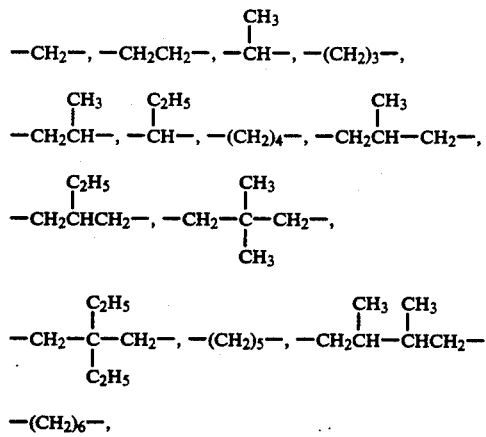

—(CH$_2$)$_7$—, —(CH$_2$)$_8$—, —(CH$_2$)$_9$— and —(CH$_2$)$_{10}$—. Preferable ones are straight or branched chain alkylene groups containing 1-6 carbon atoms such as —CH$_2$—, —CH$_2$CH$_2$—,

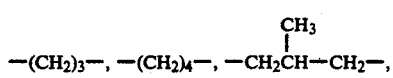

-continued

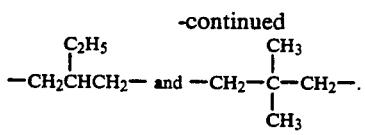

Examples of the substituents in the lower alkyl group having optionally substituent(s) are hydroxy, amino, a mono-lower alkylamino, a lower alkoxy and a halogen. The number of such substituents is one to four. Examples of the substituents in the phenyl group optionally having substituent(s) are amino, a mono- or di-lower alkylamino, a lower alkoxy and a halogen. The number of such substituents is one to five. Examples of the substituents on the straight or branched chain alkylene group containing 1-10 carbon atoms and optionally having substituent(s) are hydroxy, amino, a halogen, phenyl, benzyl, a mono-lower alkylamino, a lower alkoxy or a heterocycle. The number of such substituents is one to five. The mono-lower alkylamino group herein are exemplified with mono-$C_{1-4}$ alkylamino such as methylamino, ethylamino and propylamino. The di-lower alkylamino groups are exemplified with di-$C_{1-4}$ alkylamino such as dimethylamino and diethylamino. The lower alkoxy groups are exemplified with $C_{1-6}$ alkoxy such as methoxy, ethoxy, propoxy and hexyloxy. As the halogen atom, there is mentioned fluorine, chlorine, iodine and bromine. The heterocycle includes a 5 or 6 membered heterocycle such as thienyl, furyl, pyridyl, morpholino or thiazolyl.

The heterocyclic ring in the case where $R_2$ and $R_3$ together with the nitrogen atom to which they bond form a heterocyclic ring means a 4–7 membered heterocyclic ring having at least one nitrogen atom and optionally an oxygen and/or sulfur atoms therein. A 5 or 6 membered heterocyclic ring is normally preferable. Examples of the 5 or 6 membered heterocyclic rings are pyrrolidino, piperidino, morpholino and piperazino. These 4 to 7 membered heterocyclic rings may be substituted by one or five of substituents exemplified as those for the lower alkyl and phenyl groups.

Preferably, $R_1$ is a hydrogen atom, and $R_2$ and $R_3$ are a hydrogen atom. Preferably, X is an oxygen or sulfur atom. Preferably, Alk is for example a straight or branched chain alkylene group containing 1-6 carbon atoms such

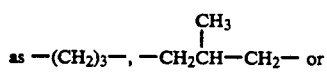

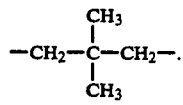

An interesting group of the compounds (I') or their salts includes a compound of the formula (I$^a$):

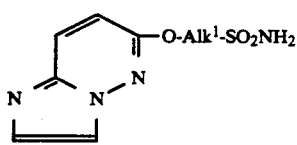

wherein Alk$^1$ is a straight or branched chain alkylene group containing 1-6 carbon atoms, or its salt; a compound of the formula (I$^b$):

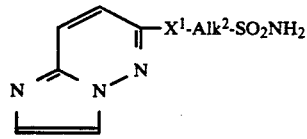

wherein $X^1$ is an oxygen or sulfur atom, and Alk$^2$ is a branched chain alkylene group containing 2-6 carbon atoms, or its salt; and a compound of the formula (I$^c$):

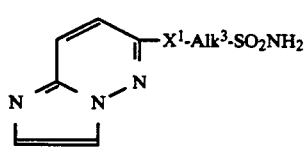

wherein $X^1$ is as defined above, and Alk$^3$ is a straight or branched chain alkylene group containing 3-5 carbon atoms, or its salt.

Specifically, Alk$^1$ may be a straight or branched chain alkylene group containing 1 to 6 atoms such as

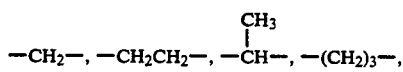

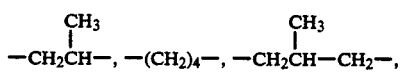

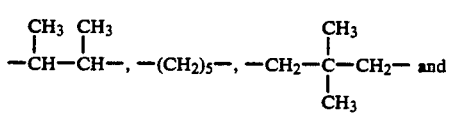

—(CH$_2$)$_6$—. Alk$^2$ may be a branched chain alkylene group containing 2 to 6 atoms such as 

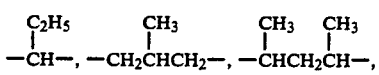

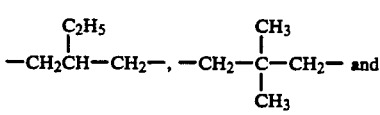

—CHCH$_2$CH$_2$CH—. Alk$^3$ may be a straight or branched chain alkylene group containing 3 to 5 atoms such as

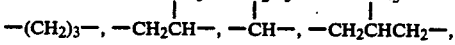

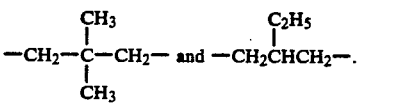

The compound (I') of this invention can be obtained by a method A) which comprises condensing a compound of the formula (II):

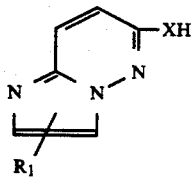

(II)

wherein $R_1$ and X are the same as defined in the formula (I'), or its salt, with a compound of the formula (III):

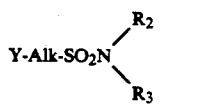

(III)

wherein $R_2$, $R_3$ and Alk are the same as defined in the formula (I'), and Y is a reactive group, or its salt, usually in the presence of a base.

Examples of the reactive groups of Y in the formula (III) are a halogen (e.g., chlorine, iodine or bromine), a $C_{1-10}$ arylsulfonyloxy (e.g., benzenesulfonyloxy or p-toylsulfonyloxy) and a $C_{1-4}$ alkylsulfonyloxy (e.g., methanesulfonyloxy). Examples of the bases are an alkaline metal hydride (e.g., sodium hydride or potassium hydride), an alkaline metal alkoxide (e.g., sodium methoxide or sodium ethoxide), a hydroxide compound (e.g., sodium hydroxide or potassium hydroxide) and a carbonate compound (e.g., sodium carbonate or potassium carbonate).

This reaction is carried out in an inert solvent such as an alcohol (e.g., methanol or ethanol), an ether (e.g., dioxane or tetrahydrofuran), an aromatic hydrocarbon (e.g., benzene, toluene or xylene), a nitrile (e.g., acetonitrile), an amide (e.g., dimethylformamide or dimethylacetamide) and a sulfoxide (e.g., dimethylsulfoxide). The reaction temperature is 10° to 200° C., preferably 50° to 100° C. The reaction time is 30 minutes to 24 hours, preferably for 1 to 6 hours. The product of this reaction can be isolated and purified by the known methods such as solvent extraction, change of basicity, redistribution, salting out, crystallization, recrystallization or chromatography.

Furthermore, the compound (I') of this invention can be obtained by a method B) which comprises condensing a compound of the formula (IV):

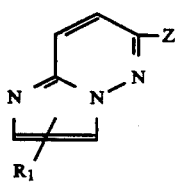

(IV)

wherein $R_1$ is the same as defined in the formula (I'), and Z is a reactive group, or its salt with a compound of the formula (V):

(V)

wherein $R_1$, $R_2$, $R_3$, X and Alk are the same as defined in the formula (I'), or its salt, usually in the presence of a base.

The reactive groups and the bases described in the aforementioned method A) are also applicable to those in this reaction, respectively.

This reaction is carried out at 10°–200° C., preferably 50°–150° C., more preferably 50°–100° C. for 30 minutes to 24 hours, preferably 1 to 10 hours in an inert solvent such as an alcohol (e.g., methanol or ethanol), an ether (e.g., dioxane, tetrahydrofuran), an aromatic hydrocarbon (e.g., benzene, toluene or xylene), a nitrile (e.g., acetonitrile), an amide (e.g., dimethylformamide or dimethylacetamide) or a sulfoxide (e.g., dimethylsulfoxide). The product can be isolated and purified by the known methods as mentioned in the method A).

Further, the compound (I') can be obtained by a method C) which comprises reacting a compound of the formula (VI):

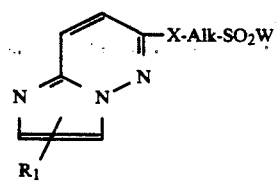

(VI)

wherein $R_1$, Alk and X are the same as defined in the formula (I'), and W is a halogen atom, or its salt with an amine of the formula (VII):

(VII)

wherein $R_2$ and $R_3$ are the same as defined in the formula (I'), or its salt.

This reaction is carried out in an inert solvent as mentioned in the above method A) or B), e.g., an alcohol (e.g., methanol, ethanol), an ether (e.g., dioxane, tetrahydrofuran), a halogenated hydrocarbon (e.g., dichloromethane, chloroform), a nitrile (e.g., acetonitrile), or a sulfoxide (e.g., dimethylsulfoxide), at −20° to 100° C., preferably at −10° to 50° C. for 30 minutes to 5 hours, preferably for 1 to 3 hours. The product can be isolated and purified by the known methods as mentioned in the above method A) or B).

The compound (I') thus obtained can be converted, if desired, to its corresponding salt by the conventional method.

The salts of the compounds (I) or (I') of this invention are suitably pharmaceutically or physiologically acceptable salts. Examples of such salts are the salts with an inorganic acid such as hydrochloric acid, sulfuric acid or phosphoric acid, or with an organic acid such as methanesulfonic acid, p-toluenesulfonic acid, lactic acid, tartaric acid or citric acid. These salts are also usable as the salts of the compounds (II), (III), (IV), (V), (VI) and (VII), which are used as the starting materials for producing the compounds (I').

As for the starting materials to be employed in the method for producing the compound (I') or salt thereof, the compounds (II) can be prepared by the method of Reference Example 1 stated below or analogous ones thereto; the compounds (III) can be prepared by the methods disclosed e.g., in Chem. Ber. 91, 2130 (1958), J. Org. Chem. 52, 2162 (1987) and Japanese Unexamined Patent Publication No. SHO 62(1987)-48687 or analogous ones thereto; the compound (IV) can be prepared by the methods disclosed e.g., in Tetrahedron 24, 239 (1968) and J. Heterocyclic Chem. 2, 53 (1965) or analogous ones thereto; the compound (V) can be prepared by converting a reactive group Y of the compound (III) into mercapto or hydroxy group in accordance with the conventional methods. The compounds (V) where X is O can be prepared by the following reaction scheme or analogous ones thereto.

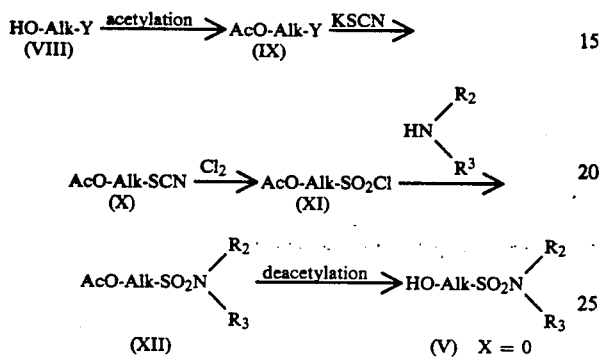

In the above formulas, Alk, Y, $R_2$ and $R_3$ have the same meanings as defined above and Ac is acetyl group. Further, the compound (VI) can be prepared by reacting a compound (II) or its salt with a compound of the formula:

wherein Y and Alk are as defined above and then halogenating thus obtained compound, or reacting a compound (IV) or its salt with a compound of the formula:

wherein X and Alk are as defined above and then halogenating thus obtained compound. And, the compound (VII) can be prepared by the method described e.g., in Comprehensive Organic Chemistry Vol. 2 (1979) or analogous ones thereto.

When the compound (I') or its physiologically acceptable salt as antiasthmatic agent is administered to mammal, e.g., human being, the dosage varies depending upon the age, body weight, status of disease, route of administration, frequency of administration, etc., but is generally 0.1 to 100 mg/kg/day, preferably 0.1 to 50 mg/kg/day, more preferably 0.5 to 10 mg/kg/day as divided into two to three times a day.

The administration route may be any of oral or parenteral one.

The compound (I') of this invention can be administered as it is, but usually in the form of a pharmaceutical preparation which is prepared together with a pharmaceutically acceptable carrier or diluent. Examples of the pharmaceutical preparations are tablets, capsules, granules, fine granules, powders, syrups, injections or inhalations. These preparations can be prepared by the conventional methods. Examples of the carriers for the oral preparations are starch, mannite, crystalline cellulose and sodium carboxymethylcellulose, which are commonly used in the pharmaceutical preparations. As the carriers to be employed for injections, there are distilled water, physiological saline solution, glucose solution and infusion agent. Other additives which are conventionally used in the pharmaceutical preparations may be suitably added to the above mentioned preparations.

REFERENCE EXAMPLE 1

Production of 6-Mercaptoimidazo[1,2-b]pyridazine

6-Chloroimidazo[1,2-b]pyridazine (13.5 g), 28 W/W % sodium methoxide-methanol solution (17.5 g) and thioacetic acid (7.0 g) were dissolved in 70 ml of methanol and this solution was heated at 150° C. in a sealed tube for 6 hours. The reaction mixture was cooled to room temperature and distilled to remove the organic solvent. The residue was washed three times with chloroform, and the insoluble material was extracted six times with 50 ml of chloroform-methanol (1:1) solution. The combined extracts were distilled to remove the organic solvent. The precipitated crystals were collected by filtration, thereby obtaining 3.7 g of 6-mercaptoimidazo[1,2-b]pyridazine.

Elementary analysis: $C_6H_5N_3S$

Calculated (%): C, 47.11; H, 3.43; N, 27.47
Found (%): C, 46.97; H, 3.25; N, 27.25

REFERENCE EXAMPLE 2

Production of 3-Hydroxy-2,2-dimethyl-1-propanesulfonamide a) A mixture of 16.7 g of 3-bromo-2,2-dimethyl-1-propanol, 14.6 g of potassium thiocyanate and 60 ml of dimethylformamide was stirred for 4 hours at 130°-140° C. The reaction solution was cooled to room temperature (hereinafter means "5°-20° C."), to which a mixture of 200 ml of diethyl ether and 200 ml of water was added. The ethereal layer was collected. The aqueous layer was extracted with 150 ml of diethyl ether. The combined ethereal layers were washed with a saturated saline, dried over anhydrous magnesium sulfate and distilled to remove the solvent. The residue was distilled under reduced pressure to obtain 12.4 g of 3-hydroxy-2,2-dimethyl-1-propylthiocyanate.

bp: 133°-134° C./4 mmHg
NMR(CDCl$_3$)δ: 1.03(6 H,s), 1.72(1 H,t,J=5 Hz), 3.46(2 H,d,J=5 Hz)

b) A mixture of 58.7 g of 3-hydroxy-2,2-dimethyl-1-propylthiocyanate, 400 ml of acetic anhydride and 400 ml of pyridine was stirred for 16 hours at room temperature. The reaction solution was concentrated under reduced pressure. The residue was dissolved in 500 ml of diethyl ether. The solution was washed in turn with 1N-hydrochloric acid, water, aqueous sodium hydrogen carbonate solution and water, and dried over anhydrous magnesium sulfate. After removing the solvent, the residue was purified by distillation under reduced pressure, thereby affording 53.2 g of 3-acetoxy-2,2-dimethyl-1-propylthiocyanate.

bp: 126°-128° C./3 mmHg
NMR(CDCl$_3$)δ: 1.09(6 H,s), 2.07(3 H,s), 3.02(2 H,s), 3.90(2 H,s)

c) Chlorine gas was bubbled in a mixture of 71.3 g of 3-acetoxy-2,2-dimethyl-1-propylthiocyanate and 550 ml of water at room temperature for 6 hours, while vigorously stirring. The reaction solution was extracted with diethyl ether (400 ml×2), and the extracts were washed with a saturated saline (300 ml×5), and dried over anhydrous magnesium sulfate. After removing the solvent, the residue was purified by distillation under reduced pressure, thereby affording 54.6 g of 3-acetoxy-2,2-dimethyl-1-propanesulfonyl chloride.

bp: 125°–126° C./0.4 mmHg
NMR(CDCl₃)δ: 1.27(6 H,s), 2.10(3 H,s), 3.86(2 H,s), 3.98(2 H,s)

d) Ammonia gas was bubbled in a solution of 20.3 g of 3-acetoxy-2,2-dimethyl-1-propanesulfonyl chloride in 300 ml of dichloromethane for an hour, keeping the reaction temperature at 13° C. or below under ice-cooling and stirring. The precipitate was filtered off, and the filtrate was concentrated and subjected to a silica gel column chromatography, eluting with methanol-chloroform (1:20). The corresponding fractions were concentrated under reduced pressure to obtain 10.8 g of 3-acetoxy-2,2-dimethyl-1-propanesulfonamide.

mp: 106°–109° C.
NMR(CDCl₃)δ: 1.19(6 H,s), 2.08(3 H,s), 3.22(2 H,s), 3.99(2 H,s)

e) To a solution of 10.0 g of 3-acetoxy-2,2-dimethyl-1-propanesulfonamide in 80 ml of methanol was added 9.2 g of 28 W/W % sodium methoxide methanol solution at room temperature with stirring. After stirring for 30 minutes, the reaction mixture was concentrated to dryness, and the residue was subjected to a silica gel column chromatography, eluting with chloroform-methanol (9:1). The corresponding fractions were concentrated to obtain 6.2 g of 3-hydroxy-2,2,-dimethyl-1-propanesulfonamide.

mp: 57°–59° C.
NMR(CDCl₃)δ: 1.00(6 H,s), 2.97(2 H,s),
3.17(2 H,d,J=5 Hz), 4.64(1 H,t,J=5 Hz),
6.69(2 H,br)
Elementary analysis: C₅H₁₃NO₃S
Calculated (%): C, 35.91; H, 7.84; N, 8.38
Found (%): C, 35.97; H, 8.02; N, 8.08

By the same method as in Reference Example 2, the following alkylsulfonamide derivatives were prepared.

3-Hydroxy-1-propanesulfonamide

NMR(CDCl₃+d₆-DMSO)δ: 2.07(2 H,m), 3.22(2 H,m),
3.71(2 H,m), 3.99(1 H,t),
6.04(2 H,s)

(R)-(-)-3-hydroxy-2-methyl-1-propanesulfonamide

[α]_D²⁴ −25.1° (c=1.0, methanol)
NMR(d₆-DMSO)δ: 1.01(3 H,d), 2.10(1 H,m), 2.71(1 H,q),
3.16(1 H,q), 3.32(2 H,m), 4.70(1 H,t),
6.77(2 H,s)

3-Hydroxy-2-ethyl-1-propanesulfonamide

NMR(CDCl₃)δ: 0.86(3 H,t), 1.47(2 H,q),
1.8–2.0(1 H,m), 2.7–3.2(2 H,m),
3.3–3.6(2 H,m), 4.59(1 H,t), 6.77(2 H,s)

REFERENCE EXAMPLE 3

Production of
3-Mercapto-2,2-dimethyl-1-propanesulfonamide a) To a solution of 5.0 g of 3-hydroxy-2,2-dimethyl-1-propanesulfonamide in 18 ml of pyridine was added 6.3 g of p-toluenesulfonyl chloride under ice-cooling and stirring. After 2 hours, the reaction mixture was poured into a mixture of 300 ml of chloroform and 100 ml of ice-water. The separated chloroform layer was washed in turn with diluted hydrochloric acid and water, dried over anhydrous magnesium sulfate and distilled under reduced pressure to obtain 8.5 g of 3-tosyloxy-2,2-dimethyl-1-propanesulfonamide.

mp: 59°–61° C.
Elementary analysis: C₁₂H₁₉NO₅S₅
Calculated (%): C, 44.84; H, 5.96; N, 4.36
Found (%): C, 44.84; H, 6.01; N, 4.27 b) A solution of 6.2 g of 3-tosyloxy-2,2-dimethyl-1-propanesulfonamide and 3.75 g of potassium thiocyanate in 30 ml of dimethylformamide was stirred at 130°–140° C. for 6 hours, and then concentrated to dryness. A mixture of dichloromethane and methanol (9:1) was added to the residue, followed by filtration to remove insoluble material. The filtrate was concentrated and the residue was subjected to a column chromatography, eluting with chloroform-ethyl acetate (2:1). The relevant fractions were concentrated to obtain 0.87 g of 3-thiocyanato-2,2-dimethyl-1-propanesulfonamide as yellow oil.

NMR(CDCl₃)δ: 1.33(6 H,s), 3.27(2 H,s), 3.31(2 H,s), 5.23(2 H,br)

c) To a solution of 5.15 g of 3-thiocyanato-2,2-dimethyl-1-propanesulfonamide in 100 ml of ethanol was little by little added 0.79 g of sodium borohydride with stirring and nitrogen gas atmosphere, taking an hour. The reaction mixture was refluxed for an hour and concentrated under reduced pressure. To the residue were added 20 ml of water and 30 ml of 1N-hydrochloric acid. The organic layer was collected, and the aqueous layer was washed with ethyl acetate (50 ml×3). The combined organic layers were dried over anhydrous magnesium sulfate and distilled to remove the solvent. The residue was subjected to a silica gel chromatography, eluting with chloroform-methanol (10:1), to obtain 0.76 g of 3-mercapto-2,2,-dimethyl-1-propanesulfonamide.

mp: 83°–86° C.
NMR(CDCl₃)δ: 1.20(6 H,s), 1.41(1 H,t), 2.69(2 H,d), 3.28(2 H,s), 4.83(1 H,br)

REFERENCE EXAMPLE 4

Production of 3-Bromo-2-ethyl-1-propanesulfonamide a) To a solution of 4.2 g of 2-ethyl-1,3-propanediol in 60 ml of dichloromethane was added 10.5 g of triphenylphosphine, to which 7.17 g of N-bromosucciniimide were little by little added under ice-cooling and stirring. The mixture was stirred for 30 minutes under ice-cooling and for an hour at room temperature, and then concentrated under reduced pressure. The residue was subjected to a silica gel column chromatography, eluting with n-hexane-ethyl acetate (7:3). The relevant fractions were concentrated to obtain 5.19 g of 3-bromo-2-ethyl-1-propanol as colorless oil.

NMR(CDCl₃)δ: 0.95(3 H,t), 1.43(2 H,q),
1.5–1.9(1 H,m), 1.60(1 H,br),
3.4–3.8(4 H,m)

b) A solution of 5.19 g of 3-bromo-2-ethyl-1-propanol and 6.02 g of potassium thiocyanate in 30 ml of dimethylformamide was stirred for 70 minutes at 100° C. To the reaction solution which was cooled was added 100 ml of ice water and the mixture was extracted with ethyl acetate (50 ml×3). The extracts were washed with water, dried and distilled to remove the solvent. The residue was subjected to a silica gel column chromatography, eluting with n-hexane-ethyl acetate. The relevant fractions were concentrated to obtain 3.30 g of 2-ethyl-3-hydroxy-1-propanethiocyanate as colorless oil.

NMR(CDCl$_3$)δ: 0.98(3 H,t), 1.50(2 H,q), 1.66(1 H,br),
1.7–2.0(1 H,m), 3.0–3.3(2 H,m),
3.5–3.9(2 H,m)

c) To solution of 3.3 g of 2-ethyl-3-hydroxy-1-propanethiocyanate and 5.96 g of triphenylphosphine in 40 ml of dichloromethane was added 4.04 g of N-bromosuccinimide under ice-cooling and stirring. The mixture was stirred for 10 minutes under ice-cooling and for an hour at room temperature and concentrated under reduced pressure. The residue was subjected to a silica gel column chromatography, eluting with n-hexane-ethyl acetate (10:1). The relevant fractions were concentrated to obtain 4.70 g of 3-bromo-2-ethyl-1-propanethiocyanate as colorless oil.

NMR(CDCl$_3$)δ: 1.00(3 H,t), 1.4–1.7(2 H,m),
1.9–2.1(1 H,m), 2.9–3.2(2 H,m),
3.4–3 8(2 H,m)

d) In a solution of 2.09 g of 3-bromo-2-ethyl-1-propanethiocyanate in 30 ml of 50% acetic acid aqueous solution was bubbled chlorine gas for an hour at room temperature with stirring. The reaction mixture was concentrated under reduced pressure and the residue was extracted with dichloromethane (50 ml×2). The extracts were dried over anhydrous magnesium sulfate and concentrated under reduced pressure. The residue was dissolved in 25 ml of dichloromethane, in which ammonia gas was bubbled for 30 minutes. The reaction solution to which 50 ml of ice water were added was extracted with dichloromethane (50 ml×2). The extracts were washed with water, dried over anhydrous magnesium sulfate and distilled to remove the solvent. The residue was subjected to a silica gel column chromatography, eluting with n-hexane-ethyl acetate (3:2). The relevant fractions were concentrated to obtain 1.58 g of 3-bromo-2-ethyl-1-propanesulfonamide as colorless oil.

NMR(CDCl$_3$)δ: 0.97(3 H,t), 1.4–1.8(4 H,m),
2.1–2.4(1 H,m), 3.5–3.9(2 H,m),
4.80(2 H,s)

By the same method as in Reference Example 4, 3-bromo-2-phenyl-1-propanesulfonamide was prepared.

NMR(CDCl$_3$)δ: 3.4–3.9(5 H,m), 4.29(2 H,s),
7.1–7.5(5 H,m)

REFERENCE EXAMPLE 5

Production of 3.6-Dichloroimidazo[1,2-b]pyridazine

6-Chloroimidazo[1,2-b]pyridazine (7.68 g) was added to 150 ml of carbon tetrachloride, to which 7.0 g of N-chlorossuccinimide were added and refluxed for 2 hours. After cooling, the precipitated crystals were filtered off. The filtrate was washed in turn with 1N-sodium hydroxide aqueous solution, 1N-hydrochloric acid and water, dried over anhydrous magnesium sulfate and distilled to remove the solvent. The residue was washed with diethyl ether to obtain 7.13 g of 3.6-dichloroimidazo[1,2-b]pyridazine.

mp: 120°–121° C.
NMR(CDCl$_3$)δ: 7.12(1 H,d), 7.75(1 H,s), 7.92(1 H,d)

EXAMPLE 1

Production of 6-(3-Sulfamoylpropylthio)imidazo [1,2-b]Pyridazine

6-Mercaptoimidazo[1,2-b]pyridazine (1.5 g) and 28 W/W % sodium methoxide-methanol solution (2.1 g) were stirred in 30 ml of methanol at 50° C. for 3 hours. The mixture was cooled to room temperature, 3.0 g of 3-aminosulfonyl-1-iodopropane were added and stirred at room temperature for 1.5 hours. The mixture was distilled to remove the solvent and the residue was subjected to a silica gel chromatography, which was eluted with successive 2 V/V % methanol-chloroform, 2.5 V/V % methanol-chloroform and 3.2 V/V % methanol-chloroform. The fractions containing the object compound were collected and concentrated. The precipitate was collected by filtration, thereby yielding 1.6 g of 6-(3-sulfamoyl-propylthio)imidazo [1,2-b]pyridazine.

Melting point (mp): 147°–148° C.
Elementary analysis: C$_9$H$_{12}$N$_4$O$_2$S$_2$
Calculated (%): C, 39.69; H, 4.44; N, 20.57
Found (%): C, 39.62; H, 4.42; N, 20.50

EXAMPLE 2

Production of 6-(3-Sulfamoylpropylthio)imidazo [1,2-b]Pyridazine

Into a solution of 3-chloropropanesulfonyl chloride (25 g) in ether (20 ml) was bubbled ammonia gas for 30 minutes under ice-cooling. Then, 50 ml of water was added to the reaction mixture. The ether layer was separated and the aqueous layer was extracted with 100 ml of ethyl acetate. The ether layer and ethyl acetate layer were combined, dried over magnesium sulfate and concentrated to dryness under reduced pressure. The residue was recrystallized from n-hexane to obtain 21 g of 3-chloropropanesulfonamide (mp: 64°–65° C.).

This product was dissolved in 150 ml of methanol and to the solution was added 150 ml of 2N-potassium hydrogen sulfide-ethanol solution. The mixture was heated at 70° C. for an hour and then distilled under reduced pressure to remove the solvent. Water (200 ml) was added to the residue. The mixture was adjusted to pH 3 with hydrochloric acid and then extracted with 200 ml of chloroform. The chloroform layer was dried over magnesium sulfate and distilled to remove the solvent, thereby yielding 10.8 g of crude 3-mercaptopropanesulfomamide.

This product was dissolved in methanol (200 ml), to which 11.8 g of 28 W/W % sodium methoxide-methanol solution and 8.0 g of 6-chloroimidazo[1,2-b]pyridazine were added. The mixture was refluxed for 3 hours, concentrated to dryness under reduced pressure. To the residue was added 100 ml of water and the aqueous solution was extracted with 100 ml of ethyl acetatetetrahydrofuran (1:1) solution. The organic layer was dried over anhydrous magnesium sulfate and distilled to remove the solvent. The residue was subjected to a silica gel column chromatography, developing with 4 V/V % methanol-chloroform. The corresponding fractions were concentrated. The residue was recrystallized from methanol to obtain 5.6 g of the title compound.

EXAMPLES 3–24

By the same method as in Example 2, the compounds of Examples 3 to 24 indicated in the Table 1 were produced.

EXAMPLE 25

Production of 6-[2-(N-cyclopropylsulfamoyl) ethylthio]imidazo[1,2-b]pyridazine

To a solution of 1.35 g of 6-chloroimidazo[1,2-b]pyridazine in 30 ml of methanol were added 1.45 g of sodium 2-mercaptoethanesulfonate and 1.80 ml of 28 W/W % sodium-methanol solution, followed by refluxing for 5 hours. The precipitated crystals were collected by filtration and washed with methanol to obtain 1.98 g of sodium 2-[(imidazo[1,2-b]pyridazin-6-yl)thio]ethanesulfonate.

mp: 263°–266° C.

This product was suspended in 10 ml of phosphorus oxychloride. The mixture was refluxed for 2 hours, and then concentrated to dryness under reduced pressure. To the residue were added 50 ml of dichloromethane, to which 2.7 g of cyclopropylamine (2.7 g) were dropwise added. The reaction mixture was stirred at room temperature for 30 minutes. After completing the reaction, 50 ml of water were added to the reaction mixture. The dichloromethane layer was separated and the aqueous layer was extracted with 50 ml of chloroform. The dichloromethane layer and the chloroform layer were combined, dried over anhydrous magnesium sulfate and evaporated to remove the solvent. The residue was subjected to a silica gel chromatography, eluted with 20 V/V % acetic acid-chloroform and then with ethyl acetate. The corresponding fractions were concentrated and the residue was recrystallized from chloroform-ether to obtain 0.30 g of the title compound.

mp: 121°–123° C.

Elementary analysis: $C_{11}H_{14}N_4O_2S_2$

Calculated (%): C, 44.28; H, 4.73; N, 18.78

Found (%): C, 43.90; H, 4.82; N, 18.82

EXAMPLES 26–28

By the same method as in Example 25, the compounds of the Examples 26–28 indicated in Table I were produced.

TABLE I

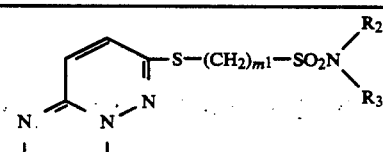

| Example No. | $m^1$ | $-N{<}^{R_2}_{R_3}$ | Melting point (°C.) | Molecular formula | Elementary analysis Calculated / Found | | |
|---|---|---|---|---|---|---|---|
| | | | | | C | H | N |
| 3 | 3 | —NHCH₃ | 114–116 | $C_{10}H_{14}N_4O_2S_2 \cdot H_2O$ | 39.46<br>39.41 | 5.30<br>5.28 | 18.41<br>18.69 |
| 4 | 3 | —NHCH₂CH₂CH₃ | 107–108 | $C_{12}H_{18}N_4O_2S_2$ | 45.84<br>45.86 | 5.77<br>5.79 | 17.82<br>17.65 |
| 5 | 3 | —NHCH(CH₃)₂ | 112–113 | $C_{12}H_{18}N_4O_2S_2$ | 45.84<br>46.10 | 5.77<br>5.77 | 17.82<br>17.89 |
| 6 | 3 | 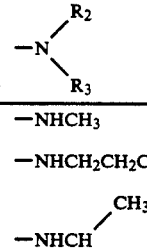 | 120–121 | $C_{12}H_{16}N_4O_2S_2$ | 46.13<br>46.08 | 5.16<br>5.16 | 17.93<br>17.86 |
| 7 | 3 | —NHCH₂CH₂OH | 119–120 | $C_{11}H_{16}N_4O_3S_2$ | 41.76<br>41.58 | 5.10<br>5.08 | 17.71<br>17.73 |
| 8 | 3 | —NHOCH₃ | 139–141 | $C_{10}H_{14}N_4O_3S_2$ | 39.72<br>39.68 | 4.67<br>4.67 | 18.53<br>18.45 |
| 9 | 3 | —N(CH₃)₂ | 110–111 | $C_{11}H_{16}N_4O_2S_2$ | 43.98<br>43.90 | 5.37<br>5.25 | 18.65<br>18.60 |
| 10 | 3 | —N(CH₂CH₃)₂ · HCl | 151–153 | $C_{13}H_{21}N_4O_2S_2Cl$ | 42.79<br>42.84 | 5.80<br>5.73 | 15.35 |
| 11 | 3 | 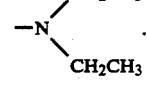 | 79–80 | $C_{14}H_{20}N_4O_2S_2$ | 49.39<br>49.57 | 5.92<br>5.91 | 16.46<br>16.52 |
| 12 | 3 | 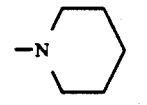 | 80–81 | $C_{13}H_{18}N_4O_3S_2$ | 45.60<br>45.59 | 5.30<br>5.30 | 16.36<br>16.27 |
| 13 | 3 | 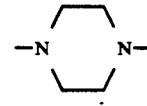 | 154–156 | $C_{14}H_{22}N_5O_2S_2Cl_3H_2O$ | 37.70<br>37.54 | 6.33<br>6.37 | 15.70<br>15.81 |

TABLE I-continued

Structure: pyridazine-S—(CH$_2$)$_{m^1}$—SO$_2$N(R$_2$)(R$_3$)

| Example No. | m$^1$ | —N(R$_2$)(R$_3$) | Melting point (°C.) | Molecular formula | Elementary analysis Calculated / Found |  |  |
|---|---|---|---|---|---|---|---|
| | | | | | C | H | N |
| 14 | 3 | —NH—C$_6$H$_5$ | 159–160 | C$_{15}$H$_{16}$N$_4$O$_2$S$_2$ | 51.70 / 51.76 | 4.63 / 4.58 | 16.08 / 16.01 |
| 15 | 3 | —NH—C$_6$H$_4$—Cl | 135–137 | C$_{15}$H$_{15}$N$_4$O$_2$S$_2$Cl | 47.05 / 47.11 | 3.95 / 4.09 | 14.63 / 14.64 |
| 16 | 3 | —NH—2,4-F$_2$C$_6$H$_3$ | 125–126 | C$_{15}$H$_{14}$N$_4$O$_2$S$_2$F$_2$ | 46.87 / 46.92 | 3.67 / 3.66 | 14.57 / 14.53 |
| 17 | 3 | —NH—3,4,5-(OMe)$_3$C$_6$H$_2$ | 179–180 | C$_{18}$H$_{22}$N$_4$O$_5$S$_2$ | 49.30 / 49.08 | 5.06 / 5.07 | 12.78 / 12.54 |
| 18 | 3 | —NH—CH$_2$-(1-naphthyl) | 113–115 | C$_{20}$H$_{20}$N$_4$O$_2$S$_2$ | 58.23 / 58.06 | 4.89 / 4.96 | 13.58 / 13.46 |
| 19 | 3 | —NHCH$_2$CH$_2$-(3-pyridyl) | 84–86 | C$_{16}$H$_{19}$N$_5$O$_2$S$_2$ | 50.91 / 50.95 | 5.07 / 5.10 | 18.55 / 18.21 |
| 20 | 3 | —NHCH$_2$CH$_2$-(1-methylpyrrol-2-yl) | 49–50 | C$_{16}$H$_{21}$N$_5$O$_2$S$_2$·H$_2$O | 48.34 / 48.48 | 5.83 / 5.74 | 17.62 / 17.63 |
| 21 | 3 | —N(piperazinyl)—CH$_2$—C$_6$H$_5$ · 2HCl | 225–227 | C$_{20}$H$_{25}$N$_5$O$_2$S$_2$·2HCl | 47.62 / 47.40 | 5.39 / 5.50 | 13.88 / 13.73 |
| 22 | 3 | —N(piperazinyl)-(3,4-methylenedioxyphenyl) · 2HCl | 203–206 | C$_{21}$H$_{25}$N$_5$O$_4$S$_2$·2HCl | 45.98 / 45.63 | 4.96 / 4.94 | 12.77 / 12.53 |

TABLE I-continued

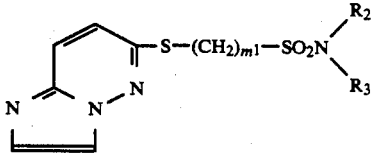

| Example No. | m¹ | −N(R₂)(R₃) | Melting point (°C.) | Molecular formula | Elementary analysis Calculated / Found C | H | N |
|---|---|---|---|---|---|---|---|
| 23 | 3 | piperazinyl-pyrimidinyl | 153–155 | $C_{17}H_{21}N_7O_2S_2$ | 48.67 / 48.70 | 5.05 / 5.00 | 23.37 / 22.94 |
| 24 | 3 | piperazinyl-pyridinyl | 121–123 | $C_{18}H_{22}N_6O_2S_2$ | 51.65 / 51.34 | 5.30 / 5.25 | 20.08 / 20.06 |
| 26 | 2 | —NH₂ | 145–147 | $C_8H_{10}N_4O_2S_2$ | 37.20 / 37.00 | 3.90 / 3.89 | 21.69 / 21.38 |
| 27 | 2 | —NHCH₃ | 76–78 | $C_8H_{12}N_4O_2S_2 \cdot \tfrac{1}{2}H_2O$ | 38.42 / 38.48 | 4.66 / 4.65 | 19.91 / 19.98 |
| 28 | 2 | —N(CH₃)₂ | 122–123 | $C_{10}H_{14}N_4O_2S_2$ | 41.94 / 41.79 | 4.93 / 4.93 | 19.56 / 19.28 |

EXAMPLE 29

Production of 6-(5-Sulfamoylpentylthio)imidazo[1,2-b]pyridazine

To a solution of 1.57 g of 5-chloropentanesulfonamide in 40 ml of methanol was added 40 ml of 2N-potassium hydrosulfide-ethanol solution, followed by heating at 70° C. for 45 minutes. To the reaction mixture was added 1.54 g of 28% sodium methoxide-methanol solution and 1.16 g of 5-chloroimidazo[1,2-b]pyridazine, which was refluxed for an hour. The reaction mixture was concentrated to dryness under reduced pressure. The residue was extracted with 40 ml of chloroform and 40 ml of 0.1N-hydrochloric acid. The aqueous layer was extracted three times with chloroform. Then the combined organic layers were dried over anhydrous magnesium sulfate and distilled to remove the solvent. The residue was subjected to a silica gel column chromatography, eluting with methanol-chloroform (1:35). The corresponding fractions were concentrated. The residue was recrystallized from methanol to obtain 0.62 g of the title compound.

mp: 120°–121° C.

Elementary analysis: $C_{11}H_{16}N_4O_2S_2$

Calculated (%): C, 43.98; H, 5.37; N, 18.65

Found (%): C, 43.97; H, 5.45; N, 18.45

The following compounds of Examples 30–34 shown in Table II were obtained by reacting 4-chlorobutanesulfonamide, 3-chloro-2-methyl-1-propanesulfonamide, 3-bromo-2-ethyl(or 2-phenyl)-1-propanesulfonamide which was obtained by the method of Reference Example 4, or 3-bromo-3-phenyl-1-propanesulfonamide which was obtained by the same method as Reference Example 4, with 6-chloroimidazo[1 2-b]pyridazine in accordance with the method described in Example 2.

EXAMPLE 35

Production of (+)-6-[(2-(S)-methyl-3-sulfamoylpropyl)thio]imidazo[1,2-b]pyridazine To a solution of 0.78 g of 2-(S)-methyl-3-chloro-1-propanesulfonamide in 20 ml of methanol was added 20 ml of 2N potassium hydrosulfide-ethanol solution, followed by refluxing at 70° C. for an hour in a stream of nitrogen. Further, to the mixture were added 1.0 g of 28% sodium methoxide-methanol solution and 0.73 g of 6-chloroimidazo[1,2-b]pyridazine, followed by refluxing for 3 hours. The reaction mixture was concentrated under reduced pressure. The residue to which 10 ml of water were added was adjusted to pH 6.0 with 1N-hydrochloric acid and then extracted with tetrahydrofuran-ethyl acetate (1:1). The extract was dried over anhydrous magnesium sulfate and distilled to remove the solvent under reduced pressure. The residue was subjected to a silica gel column chromatography, eluting with chloroform-methanol (10:1). The corresponding fractions were concentrated under reduced pressure to obtain 0.29 g of the title compound. This product was dissolved in 2 ml of hydrochloric acid-methanol, and the resultant was concentrated under reduced pressure. The residue was recrystallized from a mixture of methanol-ethyl ether to obtain 0.2 g of hydrochloride of the title compound.

mp: 154°–157° C.

$[\alpha]_D^{24} + 13.6°$ (c=1.0, water)

Elementary analysis: $C_{10}H_{14}N_4O_2S_2 \cdot HCl \cdot 0.3H_2O$

Calculated(%): C, 36.59; H, 4.79; N, 17.07

Found (%): C, 36.80; H, 4.74; N, 17.21

EXAMPLE 36

Production of (−)-6-[(2-(R)-methyl-3-sulfamoylpropyl)thio]imidazo[1,2-b]pyridazine hydrochloride The title compound was obtained from 2-(R)-methyl-3-chloro-1-propanesulfonamide in accordance with the method described in Example 35.

mp: 157°–160° C.
$[\alpha]_D^{24} -13.2°$ (c=1.0, water)

EXAMPLE 37

Production of 6-[(3-Sulfamoyl-2,2-dimethylpropyl)thio]imidazo[1,2-b]pyridazine

To a solution of 1.67 g of 2,2-dimethyl-3-thiocyanato-1-sulfonamide in 50 ml of ethanol was added by portions 0.41 g of sodium borohydride under stirring in a stream of nitrogen, followed by heating at 80°–85° C. for 1.5 hours. To the reaction mixture were added 0.62 g of 6-chloroimidazo[1,2-b]pyridazine and 0.81 ml of 28% sodium methoxide-methanol solution, followed by refluxing for 2 hours. The reaction solution was concentrated to dryness. The residue to which 30 ml of water were added was extracted with tetrahydrofuran-ethyl acetate (1:1). The extract was dried over anhydrous magnesium sulfate and distilled under reduced pressure to remove the solvent. The residue was subjected to a silica gel column chromatography, eluting with chloroform-methanol (10:1). The corresponding fractions were concentrated and the residue was then recrystallized from ethanol to obtain 0.32 g of the title compound.

mp: 198°–199° C.
Elementary analysis: $C_{11}H_{16}N_4O_2S_2$
Calculated(%): C, 43.98; H, 5.73; N, 18.65
Found (%): C, 43.94; H, 5.48; N, 18.18

EXAMPLE 38

Production of 6-[(3-Sulfamoyl-2,2-dimethylpropyl)thio]imidazo[1,2-b]pyridazine

To a solution of 0.37 g of 3-mercapto-2,2-dimethyl-1-propylsulfonamide and 0.37 g of 28% sodium methoxide-methanol solution in 50 ml of methanol was added 0.31 g of 6-chloroimidazo[1,2-b]pyridazine, followed by refluxing at 80°–85° C. for 3 hours. The reaction solution was concentrated under reduced pressure. The residue to which 30 ml of water were added was extracted with tetrahydrofuran and ethyl acetate (1:1). The extract was dried over anhydrous magnesium sulfate and distilled under reduced pressure to remove the solvent. The residue was recrystallized from ethanol to obtain 0.4 g of the title compound.

EXAMPLE 39

Production of 6-[(2,2-Dimethyl-3-sulfamoylpropyl)oxy]imidazo[1,2-b]pyridazine

To a solution of 3.5 g of 3-hydroxy-2,2-dimethyl-1-propanesulfonamide in 30 ml of DMF was added by portions 0.85 g of sodium hydride (60%, in oil) with stirring. To the mixture were added 3.18 g of 6-chloroimidazo[1,2-b]pyridazine and then 0.85 g of sodium hydride. The reaction solution was heated at 70° C. for 1.5 hours and then at 100° C. for an hour with stirring, and concentrated under reduced pressure. The residue was added into 100 ml of ice-water, extracted with ethyl acetate and tetrahydrofuran (1:1) (100 ml×4), dried over anhydrous magnesium sulfate and distilled under reduced pressure to remove the solvent. The residue was recrystallized from ethanol to obtain 5.18 g of the title compound.

mp: 165°–167° C.
Elementary analysis: $C_{11}H_{16}N_4O_3S$
Calculated (%): C, 46.47; H, 5.67; N, 19.70
Found (%): C, 46.20; H, 5.75; N, 19.44

EXAMPLE 40

Production of (+)-6-[(2-(R)-methyl-3-sulfamoylpropyl)oxy]imidazo[1,2-b]pyridazine To a solution of 0.93 g of 2-(R)-methyl-3-hydroxy-1-propylsulfonamide in 50 ml of DMF was added by portions 0.48 g of sodium hydride, followed by stirring for 30 minutes at 70° C. The mixture to which 0.93 g of 6-chloroimidazo[1,2-b]pyridazine was added was refluxed for 5 hours. After cooling, the reaction mixture was adjusted to pH 6.0 with 1N-hydrochloric acid and concentrated to dryness under reduced pressure. The residue was subjected to a silica gel column chromatography, eluting with chloroform-methanol (10:1). The corresponding fractions were collected and concentrated to obtain 1.06 g of the title compound.

$[\alpha]_D^{24} +8.7°$ (c=1.0, methanol)
Elementary analysis: $C_{10}H_{14}N_4O_3S$
Calculated (%): C, 44.43; H, 5.22; N, 20.73
Found (%): C, 44.36; H, 5.16; N, 20.70

The following compounds of Examples 41 and 42 shown in Table II were obtained by reacting 3-hydroxy-1-propylsulfonamide, or 2-ethyl-3-hydroxy-1-propylsulfonamide with 6-chloroimidazo[1,2-b]pyridazine in accordance with the method described in Example 40.

TABLE II

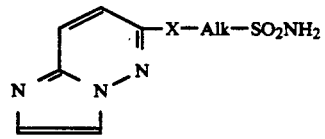

| Example No. | X | Alk | Melting point (°C.) | Molecular formula | Elementary analysis Calculated / Found | | |
|---|---|---|---|---|---|---|---|
| | | | | | C | H | N |
| 30 | S | —CH₂CH₂CH₂CH₂— | 219–221 | $C_{10}H_{14}N_4O_2S_2 \cdot HCl$ | 41.94 | 4.93 | 19.56 |
| | | | | | 41.81 | 4.86 | 19.78 |

TABLE II-continued

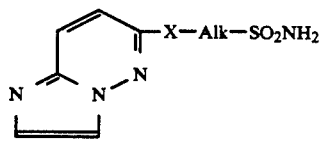

| Example No. | X | Alk | Melting point (°C.) | Molecular formula | Elementary analysis Calculated Found C | H | N |
|---|---|---|---|---|---|---|---|
| 31 | S | —CH$_2$CHCH$_2$—<br>\|<br>CH$_3$ | 208–210 | C$_{10}$H$_{14}$N$_4$O$_2$S$_2$·HCl | 37.20<br>37.55 | 4.68<br>4.55 | 17.35<br>17.49 |
| 32 | S | —CH$_2$CHCH$_2$—<br>\|<br>C$_2$H$_5$ | 120–121 | C$_{11}$H$_{16}$N$_4$O$_2$S$_2$ | 43.98<br>44.11 | 5.37<br>5.38 | 18.65<br>18.50 |
| 33 | S | —CH$_2$CHCH$_2$—<br>\|<br>C$_6$H$_5$ | 133–135 | C$_{15}$H$_{16}$N$_4$O$_2$S$_2$·HCl·0.7H$_2$O | 45.83<br>45.79 | 5.30<br>4.90 | 13.04<br>12.84 |
| 34 | S | —CHCH$_2$CH$_2$—<br>\|<br>C$_6$H$_5$ | 198–202 | C$_{15}$H$_{16}$N$_4$O$_2$S$_2$·HCl·H$_2$O | 44.71<br>44.43 | 4.75<br>4.63 | 13.91<br>13.97 |
| 41 | O | —CH$_2$CH$_2$CH$_2$— | 201–204 | C$_9$H$_{12}$N$_4$O$_3$S | 42.18<br>42.16 | 4.72<br>4.77 | 21.86<br>21.62 |
| 42 | O | —CH$_2$CHCH$_2$—<br>\|<br>C$_2$H$_5$ | 143–145 | C$_{11}$H$_{16}$N$_4$O$_3$N | 46.47<br>46.67 | 5.67<br>5.82 | 19.70<br>19.50 |

EXAMPLE 43

Production of 3-Chloro-6[(3-sulfamoylpropyl)thio]imidazo[1,2-b]pyridazine

To a solution of 1.57 g of 3-chloro-1-propanesulfonamide in 20 ml of methanol was added 20 ml of 2N-potassium hydrogensulfide-ethanol solution, followed by heating at 70° C. for 50 minutes. Then, 1.48 g of 28% sodium methoxide-methanol solution and 1.32 g of 3,6-dichloroimidazo[1,2-b]pyridazine were added to the reaction mixture and refluxed at 100° C. for 3 hours. The mixture was concentrated under reduced pressure, and to the residue was added 20 ml of water, which was adjusted to pH 7.0 with 1N-hydrochloric acid. The precipitated crystals were collected by filtration and recrystallized from methanol and ethyl ether to obtain 1.12 g of the title compound.

mp: 136°–137° C.
Elementary analysis: C$_9$H$_{11}$N$_4$O$_2$S$_2$Cl
Calculated (%): C, 35.23; H, 3.61; N, 18.26
Found (%): C, 35.12; H, 3.68; N, 18.39

EXAMPLE 44

Production of 2-chloro-6-[(sulfamoylpropyl)thio]imidazo[1,2-b]pyridazine

To a solution of 1.57 g of 3-chloro-1-propanesulfonamide in 20 ml of methanol was added 20 ml of 2N-potassium hydrogensulfide, followed by heating at 70° C. for 50 minutes. Further, 1.48 g of 28% sodium methoxide-methanol solution and 1.32 g of 2,6-dichloroimidazo[1,2-b]pyridazine [Japanese Unexamined Patent Publication No. SHO 64(1989)-38092] were added to the reaction mixture, and refluxed at 100° C. for 3 hours. The mixture was concentrated under reduced pressure. Then, the residue to which was 20 ml of water was added was adjusted to pH 7.0 with 1N-hydrochloric acid. The precipitated crystals were collected by filtration and subjected to a silica gel column chromatography, eluting with chloroform and methanol (50:1). The corresponding combined fractions were concentrated, and the residue was recrystallized to obtain 1.1 g of the title compound.

mp: 117°–118° C.
Elementary analysis: C$_9$H$_{11}$N$_4$O$_2$S$_2$Cl
Calculated (%): C, 35.23; H, 3.61; N, 18.26
Found (%): C, 35.39; H, 3.71; N, 18.25

EXAMPLE 45

Production of 3-Chloro-6-[(2,2-dimethyl-3-sulfamoylpropyl)oxy]imidazo[1,2-b]pyridazine To a solution of 1.67 g of 3-hydroxy-2,2-dimethyl-1-propanesulfonamide in 30 ml of DMF was added 0.8 g of sodium hydride, followed by heating at 70° C. for an hour. The mixture to which 1.88 g of 6-chloroimidazo 1,2-b]pyridazine was added was heated for 4.5 hours. The reaction mixture was distilled to remove the solvent under reduced pressure and 50 ml of ice-water was added to the residue. The mixture was adjusted to pH 6.0 with 1N-hydrochloric acid and then extracted with tetrahydrofuran and ethyl acetate (1:1). The extract was dried over anhydrous magnesium sulfate and distilled under reduced pressure to remove the solvent. The residue was subjected to a silica gel column chromatography, eluting with chloroform and methanol (20:1). The corresponding combined fractions were concentrated to obtain 1.56 g of the title compound.

mp: 197°–200° C.
Elementary analysis: C$_{11}$H$_{15}$N$_4$O$_3$SCl

Calculated (%): C, 41.45; H, 4.74; N, 17.58
Found (%): C, 41.21; H, 4.65; N, 17.57

EXAMPLE 46

Production of 6-[(2,2-Dimethyl-3-sulfamoylpropyl) oxy]imidazo[1,2-b]pyridazine Hydrochloride 30% Hydrochloric acid-methanol solution (5 ml) was added to a solution of 1.71 g of 6-[(2,2-dimethyl-3-sulfamoylpropyl)oxy]imidazo[1,2-b]pyridazine in 100 ml of methanol. The mixture was concentrated under reduced pressure to dryness. The residue was recrystallized from ethanol to obtain 1.7 g of the title compound.
mp: 206°–207° C.
Elementary analysis: $C_{11}H_{16}N_4O_3S \cdot HCl$
Calculated (%): C, 41.18; H, 5.38; N, 17.46
Found (%): C, 41.10; H, 5.30; N, 17.30

PREPARATION EXAMPLE a) Coated tablets

| Compound of Example 1 | 10.0 mg |
|---|---|
| Lactose | 60.0 mg |
| Cornstarch | 35.0 mg |
| Gelatin | 3.0 mg |
| Magnesium stearate | 2.0 mg |

A mixture of Compound of Example 1, lactose and cornstarch was mixed with 10% gelatin solution and passed through a filter (1 mm mesh) to obtain granules. The granules were dried at 40° C. and again screened. The resulting granules were mixed with magnesium stearate and were compressed. The resulting core tablets were coated with a sugar coating material of an aqueous suspension of sucrose, titanium dioxide, talc and acacia in accordance with conventional method. The coated tablets were glazed with yellow bees wax.

b) Tablets

| Compound of Example 1 | 10.0 mg |
|---|---|
| Lactose | 70.0 mg |
| Cornstarch | 50.0 mg |
| Soluble Starch | 7.0 mg |
| Magnesium Stearate | 3.0 mg |
| | 140.0 mg |

A mixture of compound of Example 1 and magnesium stearate was mixed with an aqueous soluble starch solution and granulated. The granules were dried and blended with lactose and cornstarch. The blend was compressed into tablets.

c) solution for injection

| Compound of Example 1 | 5.0 mg |
|---|---|
| Sodium Chloride | 20.0 mg |
| Distilled water | added to 2.0 ml |

Compound of Example 1 and sodium chloride were dissolved in distilled water, to which distilled water was added up to the prescribed concentration. The resulting solution was filtered and packed into 2 ml of ampoules under a sterile condition. The ampoules were sterilized and sealed. Each of amples contained 5mg of Compound of Example 1.

The results of pharmacological tests on representative compounds of this invention are shown below.

Method of Measurement

Effect on Bronchoconstriction Induced by Platelet Activating Factor (PAF) in Guinea Pigs Male Hartley guinea pigs (body weight 500 g) were used. The bronchoconstriction reaction in the guinea pig which has intravenously received PAF (1 μg/Kg) was measured by the Konzett-Rössler method. The trachea of the guinea pig with its back fixed was incised under anesthesia condition with urethane (intraperitoneal injection, 1.5 g/kg) and connected with an artificial respirator via a cannula. The branch of the tracheal cannula was connected with a transducer (7020 type, Ugobasile). Air was sent to the trachea at the volume of 3–7 ml/stroke, at the rate of 70 strokes/min. at load pressure of 10 cm H2O to lung and overflowed air volume was recorded with Rectegraph (Recte-Hori-8s, Sanei Sokuki) via the transducer. After the guinea pig was treated with galamine (1 mg/kg, i.v.), PAF (1 μg/kg) dissolved in a physiological saline solution was administered to the guinea pig via a jugular venous cannula and the bronchoconstriction reaction induced thereby was recorded for 15 minutes. The drug (30 mg/kg) suspended in a 5% gum arabic solution was administered orally 1 hour before the injection of PAF. The results are shown in the following Table III.

TABLE III

Effect on bronchoconstriction induced by PAF in guinea pigs

| Example No. | Inhibition (%) of PAF-induced bronchoconstriction |
|---|---|
| 1 | 71 |
| 3 | 41 |
| 6 | 47 |
| 9 | 52 |
| 19 | 41 |
| 20 | 41 |
| 25 | 47 |
| 26 | 42 |
| 29 | 51 |
| 30 | 73 |
| 31 | 74 |
| 32 | 80 |
| 33 | 52 |
| 34 | 38 |
| 35 | 79 |
| 37 | 99 |
| 39 | 72 |
| 40 | 53 |
| 41 | 66 |
| 42 | 55 |
| 43 | 54 |
| 45 | 50 |

A is clear from the above Table III, the compound (I') of the present invention possess excellent controlling effects for airway constriction and can be used as antiasthmatics.

What we claim is:

1. An imidazo[1,2-b]pyridazine compound of the formula (I):

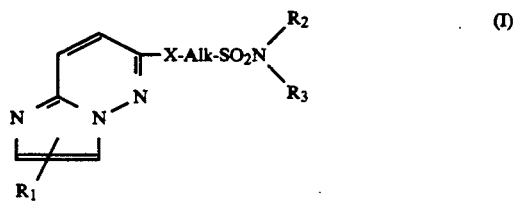

wherein R₁ is a hydrogen or halogen atom, or a lower alkyl group optionally having substituent(s) selected from the group consisting of hydroxy, amino, a mono-lower alkylamino, a lower alkoxy and a halogen, R₂ and R₃ are, independently, a hydrogen atom, a lower alkyl group optionally having substituent(s) as above, a cyclo alkyl group or a phenyl group optionally having substituent(s) selected from the group consisting of amino, a mono- or di-lower alkylamino, a lower alkoxy and a halogen, or R₂ and R₃ together with the adjacent nitrogen atom to which they bond may form a 4 to 7 membered heterocyclic ring having at least one nitrogen atom and optionally oxygen and/or sulfur atoms and optionally having substituent(s) selected from the group consisting of hydroxy, amino, mono- or di-lower alkylamino, lower alkoxy and a halogen, X is an oxygen atom or $S(O)_n$ (n=0 to 2), Alk is a straight or branched chain alkylene group containing 1-10 carbon atoms and optionally having substituent(s) selected from the group consisting of hydroxy, amino, a halogen, phenyl, benzyl, a mono-lower alkylamino, a lower alkoxy or a heterocycle, provided that X should be an oxygen atom when R₁ is a hydrogen atom, one of R₂ and R₃ is a hydrogen and the remaining one is a hydrogen atom, one of R₂ and R₃ is a hydrogen and the remaining one is a hydrogen atom or a lower alkyl group and Alk is a straight chain alkylene group containing 2-4 carbon atoms, or its pharmaceutically acceptable salt.

2. A compound of claim, 1 in which R₁ is substituted at the 2 position of imidazo[1,2-b]pyridazine ring and is a hydrogen atom or a lower alkyl group, R₂ and R₃ are, independently, a hydrogen atom, a lower alkyl group optionally having substituent(s), a cycloalkyl group or a phenyl group optionally having substituent(s) or R₂ and R₃ together with the adjacent nitrogen atom to which they bond may form a heterocyclic ring optionally having substituent(s), X is an oxygen or sulfur atom and Alk is a straight chain alkylene group containing 1-6 carbon atoms.

3. A compound of claim 1 in which (i) R₁ is a lower alkyl group substituted at the 3 position of an imidazo [1,2-b]pyridazine ring, or (ii) R₁ is a lower alkyl group having substituent(s) or a halogen atom, or (iii) X is SO or SO₂, or (iv) Alk is a straight chain alkylene group containing 1-6 carbon atoms and having substituent(s), a straight chain alkylene group containing 7-10 carbon atoms and optionally having substituent(s) or a branched chain alkylene group containing 2-10 carbon atoms and optionally having substituent(s).

4. A compound of claim 1 in which R₁ is a hydrogen atom.

5. A compound of claim 1 in which X is an oxygen atom.

6. A compound of claim 1 in which Alk is a branched chain alkylene group having 2-6 carbon atoms.

7. A compound of claim 1 in which R₂ and R₃ are a hydrogen atom.

8. A compound of claim 1 in which Alk is a branched chain alkylene group having 4 or 5 carbon atoms.

9. A compound of claim 1 which is a compound of the formula:

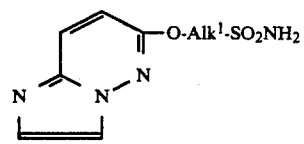

wherein Alk¹ is a straight or branched chain alkylene group containing 1-6 carbon atoms, or its salt.

10. A compound of claim 1 which is a compound of the formula:

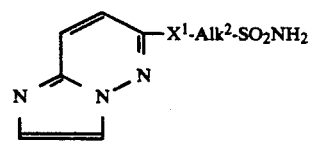

wherein Alk² is a branched chain alkylene group containing 2-6 carbon atoms and X¹ is an oxygen or sulfur atom, or its salt.

11. A compound of claim 1 which is a compound of the formula:

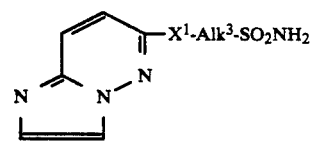

wherein Alk³ is a straight or branched chain alkylene group containing 3-5 carbon atoms, and X¹ is an oxygen or sulfur atom, or its salt.

12. A compound of claim 1 in which the lower alkyl group optionally having substituent(s) is an alkyl group containing 1-6 carbon atoms which is not substituted or substituted by hydroxy.

13. A compound of claim 1 in which the cycloalkyl group is a cycloalkyl group containing 3-6 carbon atoms.

14. A compound of claim 1 in which the phenyl group optionally having substituent(s) is a phenyl group which is not substituted or substituted by one to three of a halogen or a lower alkoxy.

15. A compound of claim 1 in which the heterocyclic ring is a 4 to 7 membered heterocyclic ring.

16. A compound of claim 1 which is 6-[(2,2-dimethyl-3-sulfamoylpropyl)oxy]imidazo[1,2-b]pyridazine or its salt.

17. A compound of claim 1 which is 6-[(2, -methyl-3-sulfamoylpropyl)thio]imidazo[1,2-b]pyridazine or its salt.

18. A method of treating asthma which comprises administering a therapeutically effective amount of a compound of the formula (I'):

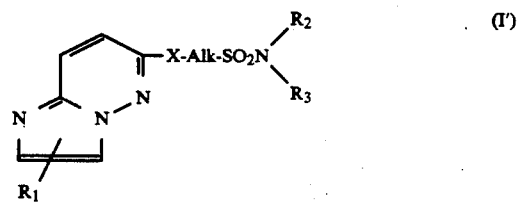

wherein $R_1$ is a hydrogen or halogen atom, or a lower alkyl group optionally having substituent(s) as defined in claim 1, $R_2$ and $R_3$ are, independently, a hydrogen atom, a lower alkyl group optionally having substituent(s) as defined in claim 1, a cycloalkyl group or a phenyl group optionally having substituent(s) as defined in claim 1 or $R_2$ and $R_3$ together with the adjacent nitrogen atom to which they bond may form a 4 to 7 membered heterocyclic ring having at least one nitrogen atom and optionally oxygen and/or sulfur atoms and optionally having substituent(s) as defined in claim 1, X is an oxygen atom or $S(O)_n$ (n=0 to 2), Alk is a straight or branched chain alkylene group containing 1-10 carbon atoms and optionally having substituent(s) as defined in claim 1, or its pharmaceutically acceptable salt, optionally together with a pharmaceutically acceptable carrier or diluent, to mammals.

19. A method of treating asthma according to claim 18, wherein the compound (I') is 6-(3-sulfamoylpropylthio) imidazo[1,2-b]pyridazine.

20. An antiasthmatic composition which comprises an effective anti-asthmatic amount of a compound of the formula (I) claimed in claim 1 or its pharmaceutically acceptable salt and a pharmaceutically acceptable carrier or diluent.

* * * * *